(12) United States Patent
Bennett (10) Patent No.: US 10,980,521 B1
(45) Date of Patent: Apr. 20, 2021

(54) TISSUE SAMPLING DEVICES AND NEEDLE HOLDERS THEREFOR

(71) Applicant: Lavon Bennett, Mesa, AZ (US)

(72) Inventor: Lavon Bennett, Mesa, AZ (US)

( * ) Notice: Subject to any disclaimer, the term of this patent is extended or adjusted under 35 U.S.C. 154(b) by 0 days.

(21) Appl. No.: 16/828,645

(22) Filed: Mar. 24, 2020

(51) Int. Cl.
*A61B 5/00* (2006.01)
*A61B 10/02* (2006.01)
*A61B 17/34* (2006.01)
*A61B 17/00* (2006.01)

(52) U.S. Cl.
CPC ...... *A61B 10/0233* (2013.01); *A61B 17/3403* (2013.01); *A61B 17/3496* (2013.01); *A61B 2010/0208* (2013.01); *A61B 2017/00407* (2013.01); *A61B 2017/347* (2013.01)

(58) Field of Classification Search
CPC .............. A61B 10/02; A61B 10/0233; A61B 2010/0208; A61B 17/3403; A61B 17/3496
See application file for complete search history.

(56) References Cited

U.S. PATENT DOCUMENTS

| | | | |
|---|---|---|---|
| 2,516,492 A | 7/1950 | Turkel | |
| 2,818,852 A | 1/1958 | Kugler | |
| 3,989,033 A | 11/1976 | Halpern et al. | |
| 4,243,048 A | 1/1981 | Griffin | |
| 4,461,305 A | 7/1984 | Cibley | |
| 4,699,154 A | 10/1987 | Lindgren | |
| 4,763,667 A | 8/1988 | Manzo | |
| 4,776,346 A | 10/1988 | Beraha et al. | |
| 4,881,551 A | 11/1989 | Taylor | |
| 4,893,635 A | 1/1990 | De Groot et al. | |
| 4,917,100 A | 4/1990 | Nottke | |
| 4,944,308 A | 7/1990 | Akerfeldt | |
| 5,014,717 A | 5/1991 | Lohrmann | |
| 5,036,860 A | 8/1991 | Leigh et al. | |
| 5,090,419 A * | 2/1992 | Palestrant | A61B 10/0275 600/567 |
| 5,127,419 A | 7/1992 | Kaldany | |
| 5,156,160 A * | 10/1992 | Bennett | A61B 10/0275 600/567 |
| 5,188,118 A | 2/1993 | Terwilliger | |
| 5,236,334 A | 8/1993 | Bennett | |
| 5,335,672 A | 8/1994 | Bennett | |

(Continued)

FOREIGN PATENT DOCUMENTS

SE 459635 B 7/1989

*Primary Examiner* — Max F Hindenburg
(74) *Attorney, Agent, or Firm* — James Sonntag; Brick Power (57) ABSTRACT

A needle holder for a tissue sampling device, such as a biopsy gun, may include a receptacle, a cradle within the receptacle, and a cover that interacts with a lock on a biopsy needle set when the cover is closed. The biopsy needle set may include a needle hub that carries a proximal end of a needle, a cannula hub that carries a proximal end of a cannula positioned over a portion of the needle, and a lock. The lock may have a locked arrangement that holds the needle hub and the cannula hub longitudinally in place relative to one another, as well as an unlocked arrangement in which the needle hub and the cannula hub may be moved toward and/or away from one another, enabling the needle to move through the cannula. Methods for obtaining samples from a body of a subject are also disclosed.

19 Claims, 7 Drawing Sheets

(56) References Cited

U.S. PATENT DOCUMENTS

| | | | |
|---|---|---|---|
| 5,336,176 A * | 8/1994 | Yoon | A61B 17/3417 |
| | | | 604/164.11 |
| 5,876,354 A * | 3/1999 | Quinn | A61B 10/0275 |
| | | | 600/562 |
| 8,790,276 B2 * | 7/2014 | Ritchart | A61B 10/0283 |
| | | | 600/566 |
| 8,986,222 B2 * | 3/2015 | Miller | A61B 10/0275 |
| | | | 600/565 |
| 2015/0088031 A1 * | 3/2015 | Paronetto | A61B 10/0233 |
| | | | 600/567 |

* cited by examiner

TISSUE SAMPLING DEVICES AND NEEDLE HOLDERS THEREFOR

TECHNICAL FIELD

This disclosure relates generally to devices for sampling tissues, such as biopsy guns. A tissue sampling device according to this disclosure includes an arrangement of concentric pistons that function in a coordinated manner to cause the needle and cannula of a biopsy needle set to obtain a sample of the tissue. A tissue sampling device according to this disclosure may include a needle holder that unlocks a complementary, locked biopsy needle set (i.e., enables its needle and cannula to slide relative to each other) when the cover is closed over the biopsy needle set. Methods of obtaining tissue samples are also disclosed.

RELATED ART

U.S. Pat. No. 5,156,160 ("the '160 patent"), U.S. Pat. No. 5,236,334 ("the '334 patent"), and U.S. Pat. No. 5,335,672 ("the '672 patent"), the entire disclosures of which are hereby incorporated herein, disclose tissue sampling devices that may be used with biopsy needle sets to obtain samples from tissues. More specifically, the foregoing patents describe tissue sampling devices that, with a single trigger of an actuator, cause the needle and cannula of a biopsy needle set to pierce tissue in a coordinated manner and to a controlled depth to obtain a sample from the tissue. The tissue sample devices of the '160, '334, and '672 patents may be used with conventional biopsy needle sets.

A conventional biopsy needle set includes a needle and a cannula. The needle of a biopsy needle set typically includes a shaft with a distal end, a proximal end, and at least one recess in the shaft at a location adjacent to the distal end. The distal end of the shaft typically comprises a tip, which may have a configuration (e.g., a point and/or one or more bevels, etc.) that enables it to pierce soft tissue. A needle hub is typically secured to the proximal end of the shaft. The cannula of a biopsy needle set typically includes a body with a tubular configuration. A distal end of the body may have a configuration (e.g., a blade edge, a point, etc.) that enables it to pierce soft tissue. A cannula hub is typically secured to a proximal end of the body. The cannula resides over at least a portion of the needle, or at least a portion of the needle resides within a lumen of the body of the cannula. In use, the needle may be introduced into soft tissue first, with a portion of the soft tissue entering into the at least one recess of the shaft of the needle. While a distal portion of the needle pierces the soft tissue, the cannula may be forced distally over the shaft of the needle, cutting the portion of the tissue within the at least one recess away from a remainder of the tissue to provide a tissue sample. The cannula and needle are then simultaneously withdrawn from the tissue, bringing the tissue sample with them.

Typically, the cannula of a conventional biopsy needle set readily slides over the shaft of the needle. Since the cannula and needle may move relative to one another, it may be difficult to ensure that they are properly positioned relative to one another during their assembly with a tissue sampling device, such as a biopsy gun. Further, since the cannula and needle of a conventional biopsy needle set can move relative to one another, conventional biopsy needle sets are typically unable to prevent inadvertent actuation of the tissue sampling device before it and the biopsy needle set are properly positioned.

SUMMARY

A tissue sampling device according to this disclosure, which may also be referred to as a "biopsy instrument" or as a "biopsy gun," may include an arrangement of concentric pistons and an actuator associated with the concentric pistons. The tissue sampling device may receive a biopsy needle set at a location adjacent to distal ends of the concentric pistons. An inner piston of the concentric pistons, which may be referred to as a "primary piston," may control movement of a needle of the biopsy needle set, while an outer piston of the concentric pistons, which may be referred to as a "secondary piston," may control movement of a cannula of the biopsy needle set. The actuator may enable an individual to control operation of (e.g., release, etc.) the primary piston, and operation of the primary piston may cause the secondary piston to operate (e.g., release the secondary piston, etc.). Thus, triggering the actuator just once may cause both the primary piston and the secondary piston to function in a concerted manner.

In some embodiments, a tissue sampling device may have a configuration that enables it to be used with a lockable biopsy needle set. A lockable biopsy needle set may include a needle and a cannula that may be locked longitudinally into place relative to each other when the biopsy needle set is not in use. Locking of the relative positions of the needle and cannula, and of the biopsy needle set, may be automatic prior to assembly of the lockable biopsy needle set with a tissue sampling device and after disassembly of the lockable biopsy needle set from the tissue sampling device.

A lockable biopsy needle set according to this disclosure includes a needle, a cannula, and a lock. The needle of the biopsy needle set includes a shaft with a distal end, a proximal end, and at least one recess in the shaft at a location adjacent to the distal end. The distal end of the shaft may comprise a tip, which may have a configuration (e.g., a point and/or one or more bevels, etc.) that enables it to pierce soft tissue. A needle hub is secured to the proximal end of the shaft.

The cannula of the biopsy needle set includes a shaft with a tubular configuration. A distal end of the shaft may have a configuration (e.g., a blade edge, a point, etc.) that enables it to pierce soft tissue. A cannula hub is secured to a proximal end of the shaft. A lock may fix the distance between the needle hub and the cannula hub may include cooperating features that lock them. The cannula resides over at least a portion of the needle, or at least a portion of the needle resides within a lumen of the shaft of the cannula.

The lock may hold the needle hub and the cannula hub in fixed positions (e.g., spaced apart positions, etc.) relative to one another. The lock may have a locked state in which it automatically fixes the relative positions of the needle hub and the cannula hub. Thus, the lock, while in the locked state, may prevent unintentional distal movement of the needle hub relative to the cannula hub and, thus, unintentional distal movement of the needle through the lumen of the shaft of the cannula. Additionally, the lock, when in the locked state, may prevent unintentional actuation of a tissue sampling device with which the lockable biopsy needle set has been assembled. The lock may also have an unlocked state in which the needle hub may move longitudinally relative to the cannula hub. In some embodiments, the locked state may be a relaxed state that automatically holds the needle hub and the cannula hub in fixed positions relative to one another, while the unlocked state of the lock may be a stressed state that temporarily allows for longitudinal movement of the needle hub relative to the cannula hub.

The lock may extend between the needle hub and the cannula hub to space them apart from each other. The needle hub may include a proximal element of the lock, while the cannula hub may include a distal element of the lock. In some embodiments, the lock of the biopsy needle set may include an elongated element and a locking element. More specifically, one of the proximal element and the distal element may comprise the elongated element, while the other of the proximal element and the distal element may comprise the locking element. The elongated element may extend from one of the needle hub and the cannula hub, toward the other. The locking element may include an aperture associated with (e.g., extending through a portion of, etc.) the other of the cannula hub and the locking hub. The aperture may be able to receive and selectively engage at least a portion of the elongated element. More specifically, the aperture may extend through a sliding element of its respective hub. Even more specifically, the sliding element may be biased (e.g., spring-biased, etc.) to force an edge of the aperture into a corresponding groove of the elongated element (e.g., a groove between adjacent teeth, etc.), thereby locking the needle hub and the cannula hub into spaced apart relation to one another.

A tissue sampling device may receive the lockable biopsy needle set and, upon receiving the lockable biopsy needle set, place the lock in the unlocked state, thereby unlocking the lockable biopsy needle set. In some embodiments, assembly of the lockable biopsy needle set with the tissue sampling device may automatically place the lock in the unlocked state, or unlock the lockable biopsy needle set. In other embodiments, the tissue sampling device may enable an individual (e.g., a healthcare professional who operates the tissue sampling device, etc.) to selectively unlock a lockable biopsy needle set that has been assembled with the tissue sampling device.

In various embodiments, a tissue sampling device according to this disclosure may include a needle holder, which may be more simply referred to as a "holder." The needle holder may be fixedly secured in place relative to the distal ends of the concentric pistons of the tissue sampling device. The needle holder may facilitate the ready assembly of a biopsy needle set (e.g., a lockable biopsy needle set, a conventional biopsy needle set, etc.) with and disassembly of the biopsy from the tissue sampling device. More specifically, the needle holder may receive and position a biopsy needle set in place relative to distal ends of the concentric pistons of the tissue sampling device so the tissue sampling device and the biopsy needle set can be used to obtain a sample of a tissue of interest. In embodiments where a lockable biopsy needle set or, more specifically, a locked biopsy needle set is assembled with the needle holder, assembly of the locked biopsy needle set with the needle holder may place the lock of the lockable biopsy needle set in its unlocked state.

The needle holder may include a receptacle, a cradle within the receptacle, and a cover, or lid. The receptacle may receive at least the needle hub, the cannula hub, and the lock of the lockable biopsy needle set. The cradle may also receive and ensure that the needle hub and the cannula hub and, thus, the needle and cannula are properly positioned. The cover may close over the receptacle and any biopsy needle set carried thereby in a manner that places the lock in the unlocked state and enables the needle hub to move relative to the cannula hub and the needle to move through the cannula. Continuing with the above-described embodiment of a locking element that comprises a biased sliding element, when the cover of the needle holder is closed over the receptacle, the cradle, and the hubs of the lockable biopsy needle set therein, it may depress the sliding element of the hub, causing it to move relative to a remainder of the hub and causing the edge of the aperture to disengage the groove of the elongated element of the lock.

Methods of obtaining tissue samples include use of a tissue sampling device according to this disclosure. Such a method may include use of a lockable biopsy needle set. More specifically, a lockable biopsy needle set, in its locked state, may be assembled with a tissue sampling device. Upon assembly the lockable biopsy needle set with the tissue sampling device, its lock may be disengaged, placing the lockable biopsy needle set in an unlocked state. By placing the lockable biopsy needle set in its unlocked state, it may be used to obtain a sample of a targeted tissue. More specifically, the tissue sampling device may be used to actuate the lockable biopsy needle set in a manner that causes it to obtain a sample of the targeted tissue.

The tissue sampling device may be used in any of a variety of contexts, including, without limitation, manually or remotely. As an example of remote use, a tissue sampling device may be used in connection with an imaging device (e.g., a magnetic resonance imaging (MM) device, a computed tomography (CT) device, etc.) while imaging a tissue of interest to identify a specific location of the tissue that is to be sampled.

Other aspects of this disclosure, as well as features and advantages of various aspects of the disclosed subject matter, should become apparent to those of ordinary skill in the art through consideration of the ensuing description, the accompanying drawings, and the appended claims.

DETAILED DESCRIPTION

With reference to FIGS. 1-6, an embodiment of a biopsy needle set 10 is illustrated. The biopsy needle set 10 includes a needle 20 and a cannula 60. A configuration of the biopsy needle set 10 may enable the needle 20 and the cannula 60 to be fixed, or secured, longitudinally in place relative to each other. More specifically, a configuration of the biopsy needle set 10 may enable the needle 20 to be locked into one or more positions along the length of the cannula 60. Even more specifically, the biopsy needle set 10 may include a lock 40 that fixes, secures, or locks the needle 20 into place along the length of the cannula 60.

Figure 1:
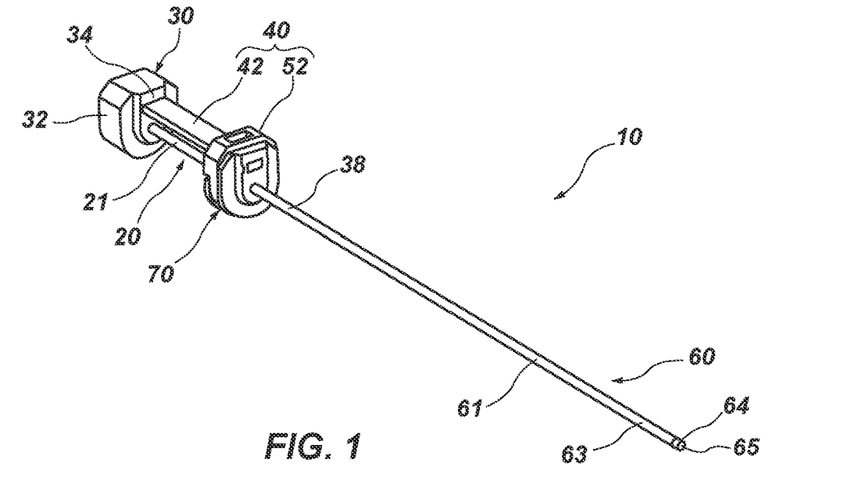
FIG. 1 is a perspective view of an embodiment of a lockable biopsy needle set according to this disclosure, with the lockable biopsy needle set including a needle, a cannula, and a lock, illustrating a locked relationship between the needle and the cannula.
Figure 1A:
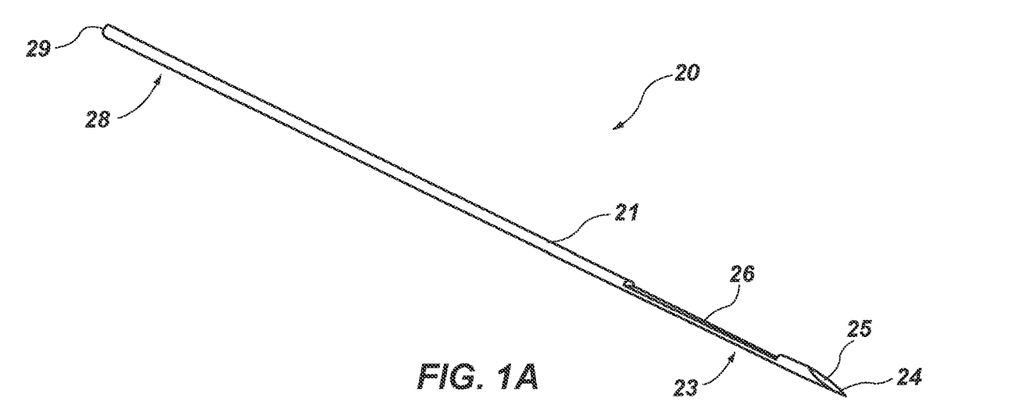
FIG. 1A shows a needle of the lockable biopsy needle set of FIG. 1.

As shown in FIG. 1A, the needle 20 includes a shaft 21 with a distal portion 23, a distal tip 24, a proximal portion 28, and a proximal end 29. The shaft 21 may be solid. The distal tip 24 may comprise a tapered point 25 that enables the needle 20 to pierce a subject's skin, as well as tissues and/or pathologies beneath the subject's skin, including a targeted tissue or pathology beneath the subject's skin. A receptacle 26, or "notch," may be formed in the shaft 21 adjacent to the distal tip 24. The receptacle 26 may receive tissue or pathology within which the distal tip 24 has been introduced.

Figure 2:
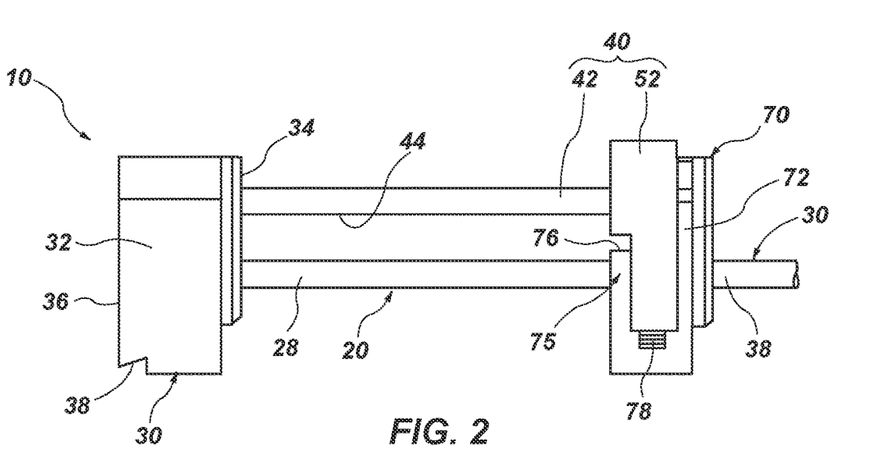
FIG. 2 is a side view of the embodiment of lockable biopsy needle set shown in FIG. 1, with the needle and the cannula in the locked relationship.
Figure 3:
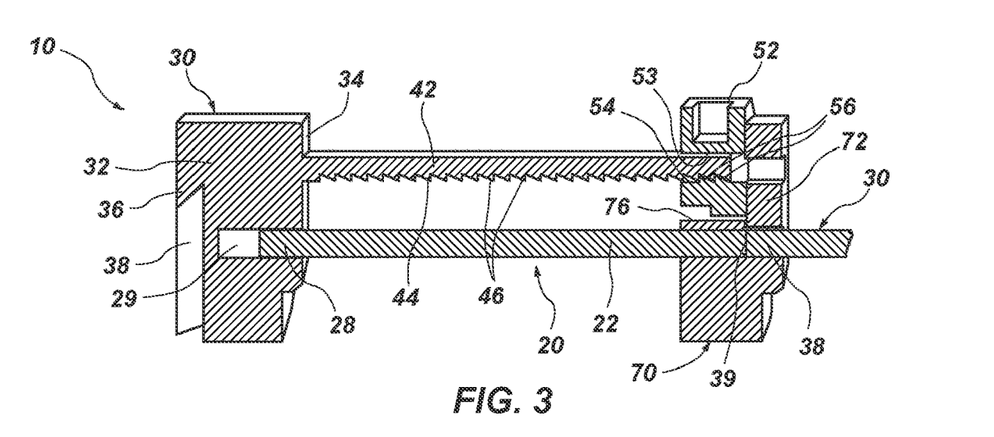
FIG. 3 is a cross-section taken through a longitudinal axis of the needle and the cannula of the lockable biopsy needle set shown in FIG. 1, with the needle and the cannula in the locked relationship.

With returned reference to FIGS. 1-3, a needle hub 30 may be carried by and secured to the proximal portion 28 of the shaft 21 of the needle 20, over the proximal end 29 of the shaft 21. The needle hub 30 may comprise a body 32 with a receptacle 33 that receives the proximal end 29 of the shaft 21 of the needle 20. The proximal end 29 may be secured within the receptacle 33 in any suitable manner (e.g., mechanically; with an adhesive, such as an epoxy; etc.). The body 32 of the needle hub 30 may also be configured, or shaped, to cooperate with an inner piston, or primary piston, of a compatible tissue sampling device (not shown). A configuration of the body 32 of the needle hub 30 may also enable it to travel forward (i.e., distally) and backward (i.e., proximally) through a needle holder 110 (FIGS. 7-14).

Additionally, a proximal side 36 of the needle hub 30 may have an configuration that enables it to be engaged by the primary piston 220 (FIGS. 7, 9, and 12) of a tissue sampling device 200 (FIGS. 7-12). More specifically the proximal side 36 of the needle hub 30 may include a receptacle 38 that can be engaged by a distal end of the primary piston 220. As illustrated, the receptacle 38 may comprise a dovetailed recess, which can receive a dovetailed distal end of the primary piston 220 of the tissue sampling device 200.

A proximal element 42 of a lock 40 may extend from a distal side 34 of the body 32 of the needle hub 30. The proximal element 42 may comprise an elongated element, which may be referred to as a "locking bar." An elongated proximal element 42 may be spaced apart from but oriented parallel or substantially parallel (e.g., accounting for manufacturing and/or assembly tolerances, etc.) to the needle 20. Such an arrangement may maintain alignment of the needle 20 and the cannula 60 and, thus, prevent the needle 20 and the cannula 60 from twisting relative to each other.

The proximal element 42 of the lock 40 may cooperate with a distal element 52 of the lock 40. The distal element 52, which may be referred to as a "locking clip," may include an aperture 53 that receives the proximal element 42 of the lock 40. A distal end 48 of the proximal element 42 may have a configuration (e.g., a compressible clip with a central slot and outwardly facing prongs, etc.) that enables it to slide distally through the aperture 53, while preventing the distal element 52 from sliding back off of the distal end 48 of the proximal element 42. Thus, a configuration of the distal end 48 of the proximal element 42 may prevent unintentional disassembly of the proximal element 42 and the distal element 52 of the lock 40.

As illustrated, the proximal element 42 may include a surface 44 (e.g., a bottom surface in the depicted embodiment and orientation, etc.) that defines or carries a series of teeth 46.

Figure 6:
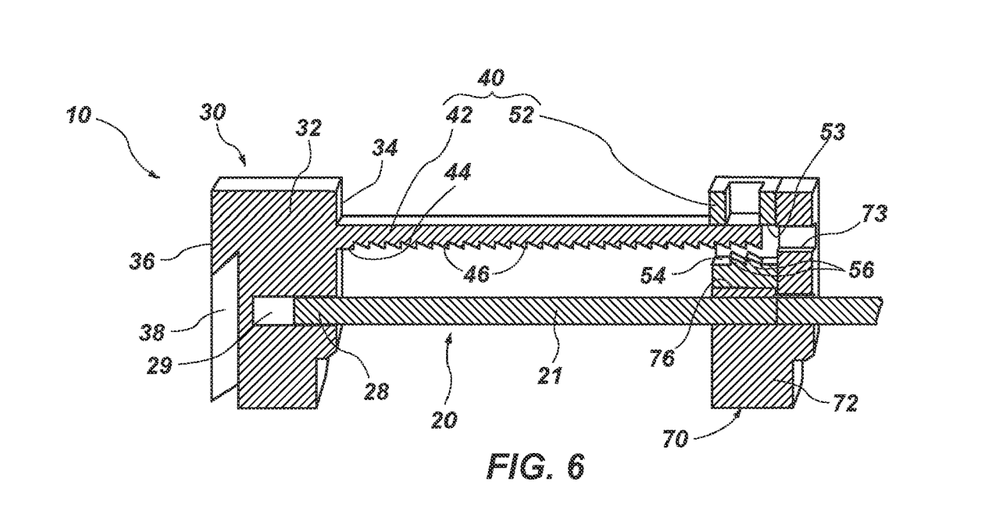
FIG. 6 is a cross-section taken through a longitudinal axis of the needle and the cannula of the lockable biopsy needle set shown in FIG. 1, with the needle and the cannula in the unlocked relationship.

A surface 54 of the distal element 52 may define or carry a series of teeth 56. The teeth 56 of the distal element 52 may complement and be able to engage the teeth 46 of the proximal element 42. When the proximal element 42 is properly inserted into the aperture 53, the surface 54 and the teeth 56 thereon may face, or oppose, the surface 44 of the distal element 42 and the teeth 46 thereon (e.g., the surface 54 may comprise an upwardly facing surface at a bottom of the distal element 52 in the depicted embodiment and orientation, etc.). When the distal element 52 is in an unlocked orientation, as shown in FIG. 6, the teeth of 56 of the distal element 52 do not engage, or are disengaged from, the teeth 46 of the proximal element 42; thus, the proximal element 42 may move distally and/or proximally relative to the distal element 52. When the distal element 52 is in a locked orientation, as shown in FIG. 3, the teeth 56 of the distal element 52 may engage teeth 46 of the proximal element 42, preventing the proximal element 42 and, thus, the needle hub 30 from distal and/or proximal movement relative to the distal element 52.

Figure 4:
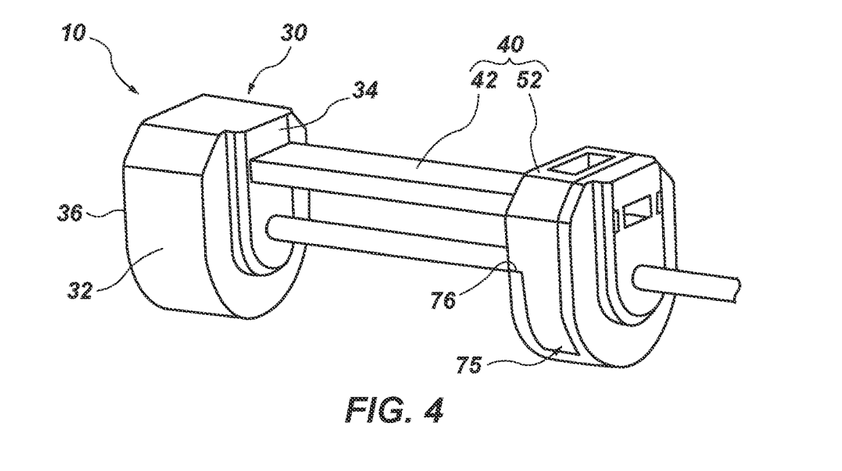
FIG. 4 is a perspective view of the embodiment of lockable biopsy needle set shown in FIG. 1, illustrating an unlocked relationship between the needle and the cannula.
Figure 5:
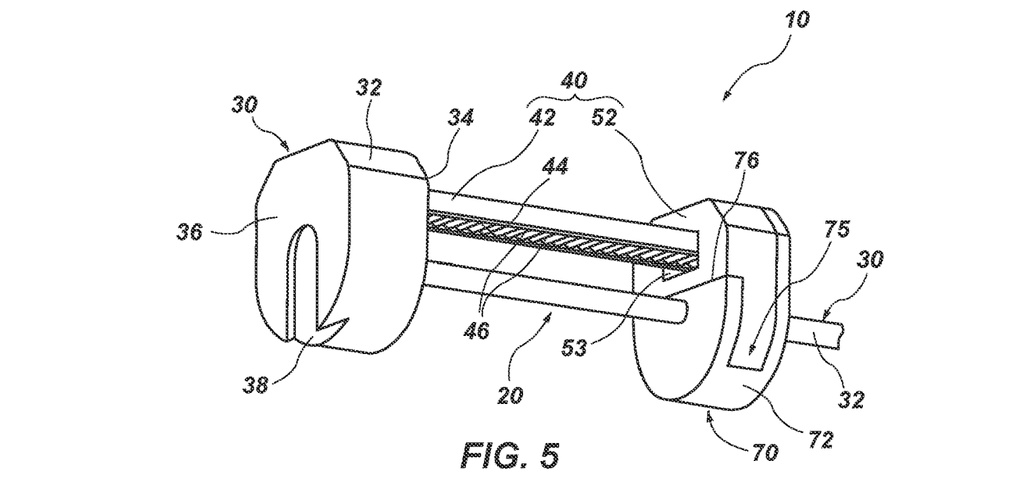
FIG. 5 is a side view of the embodiment of lockable biopsy needle set shown in FIG. 1, with the needle and the cannula in the unlocked relationship.

The distal element 52 of the lock 40 may be assembled with a body 72 of a cannula hub 70 at a proximal end 69 of a shaft 61 of the cannula 60. More specifically, the distal element 52 may be selectively positioned between the unlocked orientation and the locked orientation relative to the cannula hub 70. FIGS. 4-6 show an embodiment of the unlocked orientation of the distal element 52 of the lock 40 relative to the cannula hub 70 (e.g., a lowered position relative to the cannula hub 70 in the depicted embodiment and orientation, etc.). FIGS. 1-3 show an embodiment of the locked orientation of the distal element 52 of the lock 40 relative to the cannula hub 70 (e.g., a raised position relative to the cannula hub 70 in the depicted embodiment and orientation, etc.). Even more specifically, the distal element 52 of the lock 40 may be coupled to the body 72 of the cannula hub 70 in a manner that enables the distal element 52 to slide relative to the body 72 (e.g., up and down in the depicted embodiment and orientation, etc.).

In addition to including a proximal end 69, the shaft 61 of the cannula 60 may include a proximal portion 68, a distal portion 63, and a distal tip 64, as well as a lumen 62 within the shaft 61. The proximal portion 68 of the shaft 61 of the cannula 60 may carry the cannula hub 70. The distal tip 64 of the shaft 61 may comprise a tapered point 65 that enables the cannula 60 to pierce the subject's skin, as well as tissues and/or pathologies beneath the subject's skin, including a targeted tissue or pathology beneath the subject's skin. The distal tip 64 may also include a blade 66, which may cut through tissue and/or pathology within the receptacle 26 in the distal portion 23 of the shaft 21 of the needle 20. The lumen 62 may extend through an entire length of the shaft 61. A configuration and dimensions of the lumen 62 may enable it to receive the needle 20 and enable the needle 20 to move along the lumen 62.

The body 72 of the cannula hub 70 may have a configuration, or a shape, that enables it to cooperate with a corresponding element of a cradle 140 (FIGS. 15-17), which in turn moves with an outer piston, or a secondary piston, of a compatible tissue sampling device (not shown). A configuration of the body 72 of the cannula hub 70 may also enable it to travel forward (i.e., distally) and backward (i.e., proximally) through a needle holder 110 (FIGS. 7-14).

The body 72 of the cannula hub 70 may include an aperture 73. The aperture 73 of the body 72 of the cannula hub 70 may be aligned with the aperture 53 through the distal element 52 of the lock 40. Like the aperture 53 through the distal element 52 of the lock 40, the aperture 73 through the body 72 of the cannula hub 70 may receive a portion of the proximal element 42 of the lock 40. When the distal element 52 of the lock 40 is in the locked orientation, the aperture 73 through the body 72 of the cannula hub 70 may receive a portion of the proximal element 42, and the proximal element 42 may freely travel distally and proximally through the aperture 73.

In addition, the body 72 of the cannula hub 70 may include a seat 75 that accommodates the distal element 52 of the lock 40. The seat 75 may include a coupling feature (not shown) that cooperates with a complementary coupling feature of the distal element 52 to couple to the distal element 52 to the body 72 of the cannula hub 70. More specifically, the cooperating coupling features may enable the distal element 52 to slide from its unlocked orientation to its locked orientation. A base surface 76 of the seat 75 may support the distal element 52 while the distal element 52 is in its unlocked orientation. The base surface 76 of the seat 75 and/or the cooperating coupling elements may limit the extent to which the distal element 52 may slide while it is placed in its unlocked orientation. A spring 78 associated with the seat 75 may force, or bias, the distal element 52 away from the base surface 76 and, thus, into the locked orientation. Thus, when no force is applied to the distal element 52 of the lock to force it toward the base surface 76 and, thus, into the unlocked orientation, the spring 78 will hold the distal element 52 in the locked orientation. The spring 78 may comprise a coiled spring, a torsion spring, a living spring that is molded as a part of the distal element 52 of the lock 40 and/or the body 72 of the cannula hub 70, or any other suitable embodiment of spring.

FIGS. 1-3 show the biopsy needle set 10 with the needle 20 and the cannula 60 in a locked arrangement, which may be established when the distal element 52 of the lock 40 is placed in its locked orientation against the proximal element 42 of the lock 40, for example, as the teeth 56 of the distal element 52 engage the teeth 46 of the proximal element 42. When the biopsy needle set 10 is in the locked arrangement, the lock 40 may fix, secure, or lock the needle 20 into place along the length of the cannula 60 of the biopsy needle set 10. The biopsy needle set 10 may be placed in the locked arrangement when it is not being used; for example, during storage or transportation of the biopsy needle set 10, prior to assembly of the biopsy needle set 10 with a tissue sampling device (e.g., a tissue sampling device according to the '160 patent, the '334 patent, the '672 patent, etc.), after disassembly of the biopsy needle set 10 from the tissue sampling device, etc. In some embodiments, a configuration of the lock 40 may enable it to automatically fix, secure, or lock the needle 20 and the cannula 60 into place relative to one another prior to assembly of the biopsy needle set 10 with the tissue sampling device and/or following disassembly of the biopsy needle set 10 from the tissue sampling device.

A configuration of the lock 40 may also enable it to release or unlock the relative positions of the needle 20 and the cannula 60, placing the biopsy needle set 10 in an unlocked arrangement, such as that depicted by FIGS. 3-6. The lock 40 may place the biopsy needle set 10 in the unlocked arrangement upon assembly of the biopsy needle set 10 with the tissue sampling device. In some embodiments, a configuration of the lock 40 may enable it to automatically place the biopsy needle set into the unlocked arrangement, releasing of unlocking the relative positions of the needle 20 and the cannula 60.

Figure 7:
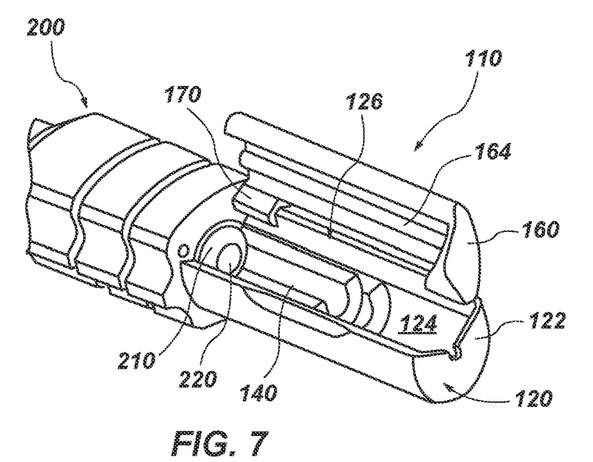
FIG. 7 is a perspective view of an embodiment of a needle holder according to this disclosure, with the needle holder including a receptacle, a cradle within the receptacle, and a cover, and FIG. 7 depicting the cover in an open orientation away from, or exposing an opening of the receptacle and the cradle within the receptacle.
Figure 8:
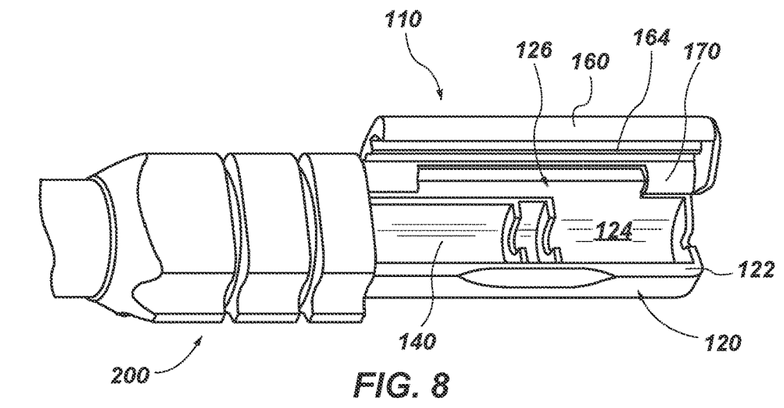
FIG. 8 is a top view of the embodiment of needle holder shown in FIG. 7, depicting the cover in the open orientation relative to the receptacle.
Figure 9:
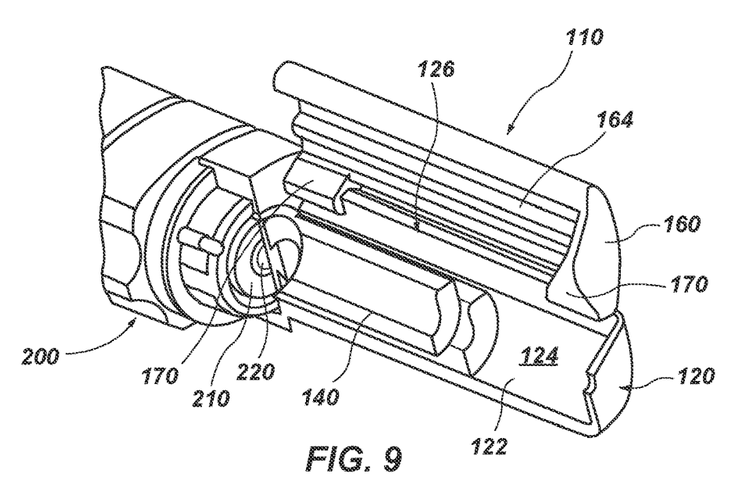
FIG. 9 is a cross-sectional representation of the needle holder shown in FIG. 7, taken along a length of the needle holder and depicting the cover in the open orientation relative to the receptacle.
Figure 10:
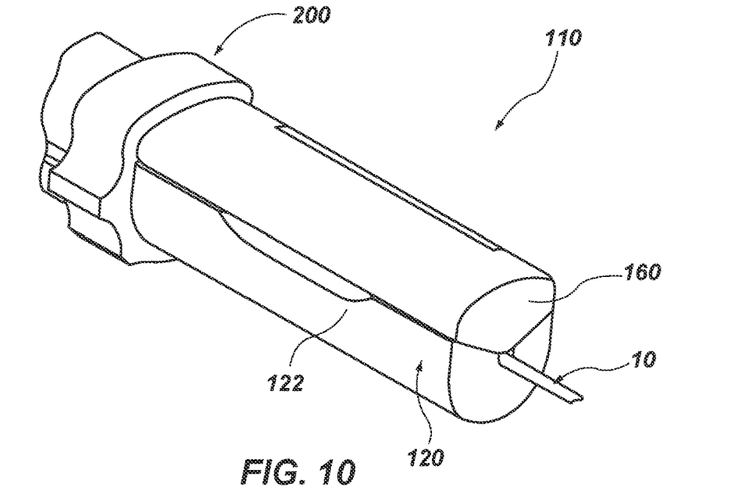
FIG. 10 is a perspective view of the embodiment of needle holder shown in FIG. 7, depicting the cover in a closed orientation over an opening that provides access to the receptacle and the cradle.
Figure 11:
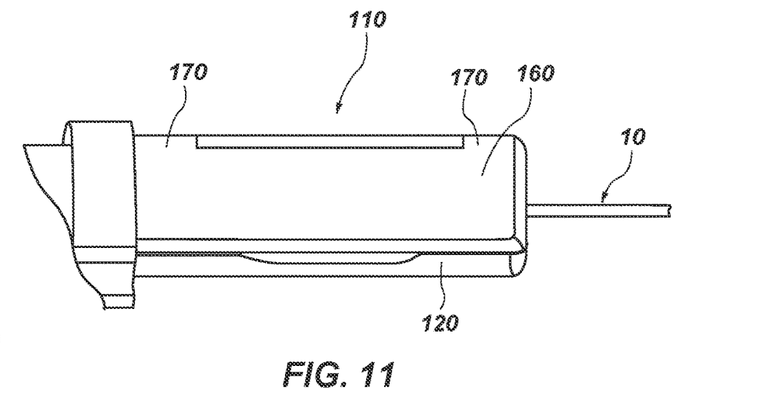
FIG. 11 is a top view of the embodiment of needle holder shown in FIG. 7, depicting the cover in the closed orientation over the opening that provides access to the receptacle and the cradle.
Figure 12:
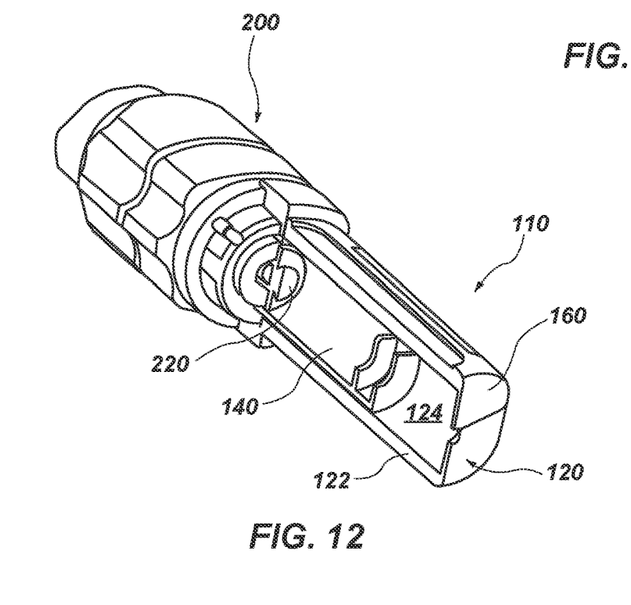
FIG. 12 is a perspective cutaway representation of the needle holder shown in FIG. 7, taken along a length of the needle holder and depicting the cover in the closed orientation over the opening of the receptacle and the cradle.

A tissue sampling device may include a needle holder 110 that can removably receive the biopsy needle set 10. FIGS. 7-12 illustrate an embodiment of needle holder 110. That needle holder 110 includes a receptacle 120, a cradle 140, and a cover 160. The receptacle 120 holds the cradle 140. The cover 160 that provides selective access to an interior of the cradle 140. FIGS. 7-9 show an example of an open orientation of the cover 160 relative to the receptacle 120. FIGS. 11-14 depict an example of a closed orientation of the cover 160 over the receptacle 120.

Referring to FIGS. 7-9, the receptacle 120 of the needle holder 110 includes a body 122. The body 122 defines an interior 124 of the receptacle 120. An opening 126 through the body 122 (e.g., through a front of the body 122, etc.) may provide access to the interior 124 of the receptacle 120. In various embodiments, the opening 126 may facilitate the introduction of a biopsy needle set 10 (FIGS. 1-6) into the interior 124 of the receptacle 120.

In its open orientation, the cover 160 may be moved to a position that provides access to the opening 126 and, thus, to the interior 124 of the receptacle 120. In some embodiments, the cover 160 may be hingedly associated with the body 122 of the receptacle 120. More specifically, one or more hinges 170 (e.g., a living hinge, etc.) may secure the cover 160 to the body 122 of the receptacle 120 and enable movement of the cover 160 between the open orientation illustrated by FIGS. 7-9 and the closed orientation depicted by FIGS. 10-12.

The lock 40 of the biopsy needle set 10 may ensure that the needle hub 30 and the cannula hub 70 are spaced a sufficient distance from one another to facilitate their introduction into the receptacle 120 of the needle holder 110. In addition, the lock 40 may ensure that the receptacle 26 in the shaft 21 of the needle 20 may remain within the lumen 62 that extends through the shaft 61 of the cannula 60 (FIGS. 1 and 1A) until extension of the distal tip 24 of the needle 20 beyond the distal tip 64 of the cannula 60 is desired.

As the cover 160 is closed over the interior 124 of the receptacle 120, a lock-engaging feature 164, such as the depicted rib, that protrudes from an interior surface 162 of the cover 160 may engage and depress the distal element 52 of the lock 40. As closure of the cover 160 overcomes the biasing force of the spring 78 associated with the distal element 52 of the lock 40, the distal element 52 is moved from its locked orientation to its unlocked orientation, in which teeth 56 of the distal element 52 disengage teeth 46 of the proximal element 42 of the lock 40. With the distal element 52 of the lock 40 in the unlocked orientation, the needle hub 30 and, thus, the needle 20 may move (e.g., distally, etc.) relative to the cannula hub 70 and the cannula 60.

With returned reference to FIGS. 7-9, a primary piston 220 and a secondary piston 210 of a tissue sampling device 200 may extend distally into the interior 124 of the receptacle 120 through a proximal end of the receptacle 120. The primary piston 220 may be selectively extended distally into the interior 124 to force the needle hub 30 (FIGS. 1-6) and, thus, the needle 20 (FIGS. 1-6) distally. In some embodiments, such as that depicted by FIGS. 7 and 9, a distal end of the primary piston 220 may comprise a dovetailed protrusion, which may be received by a complementary dovetailed receptacle 38 in a proximal side 36 of a needle hub 30, such as that depicted by FIGS. 5 and 6.

A distal end of the secondary piston 210 may engage a proximal side of the cradle 140. Without limitation, the distal end of the secondary piston 210 may include threads that complement threads at or in a proximal side of the cradle 140, which may enable the cradle 140 to be screwed onto the distal end of the secondary piston 210.

The cradle 140 may be located within a base 125 of the interior 124 of the receptacle 120 and may slide along a length of the interior 124 of the receptacle 120 (i.e., longitudinally). The cradle 140 may have a configuration, or a shape, that enables it to engage (e.g., receive, etc.) a portion of the cannula hub 70 (FIGS. 1-6) and hold the cannula hub 70 in place relative to the cradle 140. The cradle 140 may interact with the secondary piston 210 of the tissue sampling device 200. More specifically, movement of the cradle 140 may be controlled as the secondary piston 210 is introduced into the interior 124 of the receptacle 120 and forces the cradle 140 distally, which in turn carries the cannula hub 70 and the cannula 60 (FIGS. 1-6) distally.

The cradle 140 may also receive the needle hub 30 (FIGS. 1-6) in a manner that facilitates longitudinal movement of the needle hub 30 relative to the cradle 140.

Figure 13:
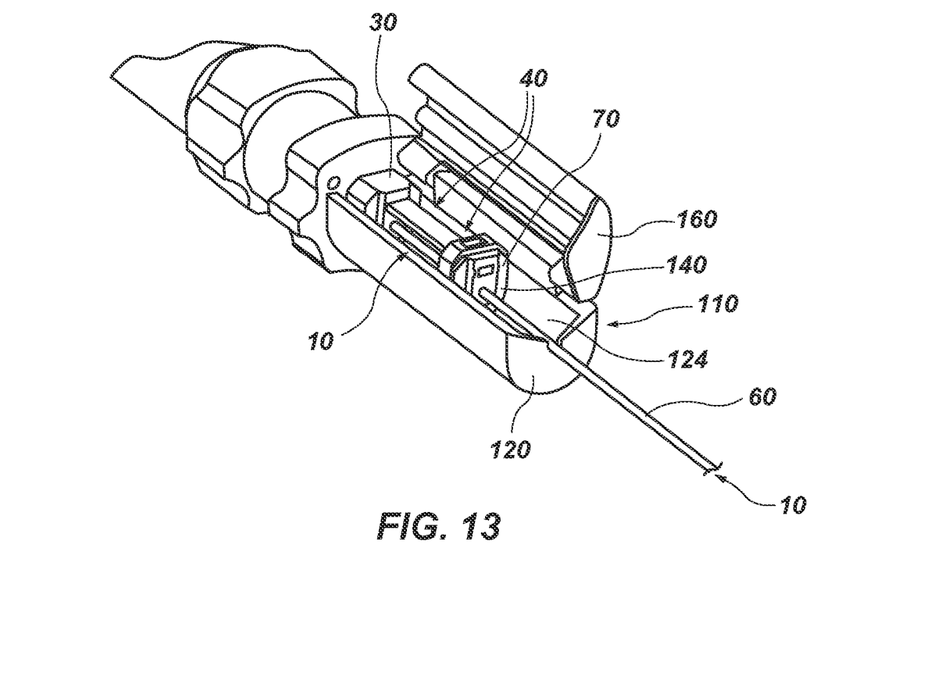
FIG. 13 is a perspective view of an assembly including the embodiment of lockable biopsy set shown in FIG. 1 within the cradle of the needle holder shown in FIG. 7, depicting the cover of the needle holder in the open orientation relative to the cradle of the needle holder and the lock of the lockable biopsy needle set in a locked position that prevents the needle of the lockable biopsy needle set from moving relative to the cannula of the lockable biopsy needle set.
Figure 14:
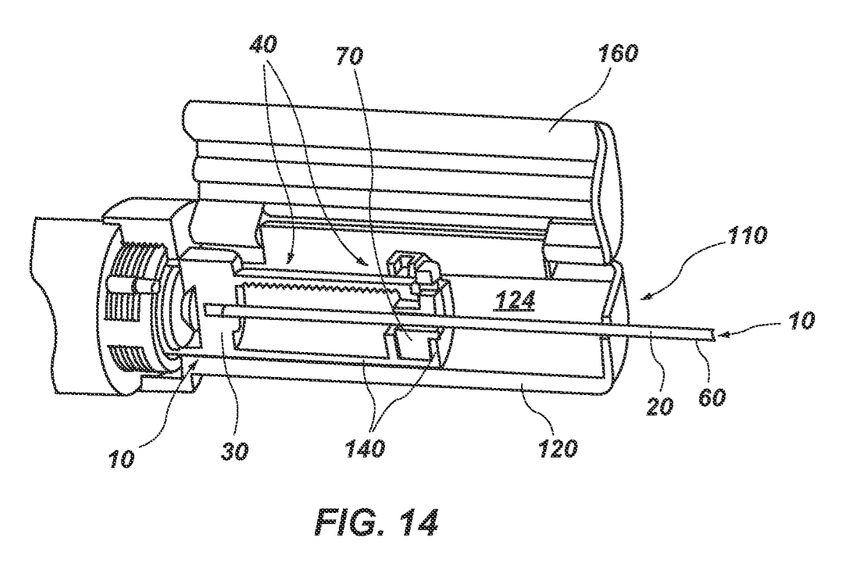
FIG. 14 is a cross-sectional representation of the assembly shown in FIG. 13, with the cover of the needle holder in the open orientation and the lock of the lockable biopsy needle in the locked position.

Looking now to FIGS. 13 and 14, the biopsy needle set 10 (FIGS. 1-6) and the needle holder 110 (FIGS. 7-12) are depicted in an assembled relationship with the cover 160 of the needle holder 110 in its open orientation. In the assembled relationship depicted by FIGS. 15-17, the cradle 140 is in a cocked position (i.e., located proximally) within the interior 124 of the receptacle 120, as it would be prior to use of a tissue sampling device of which the needle holder 110 is a part or to which the needle holder 110 has been coupled and prior to use of the biopsy needle set 10. With the cover 160 in its open orientation and the cradle 140 in the cocked position, the receptacle 120 can receive the biopsy needle set 10, and the biopsy needle set 10 may remain in its locked arrangement, which will prevent premature triggering of the tissue sampling device and premature actuation of the needle 20 and the cannula 60 of the biopsy needle set 10.

Figure 15:
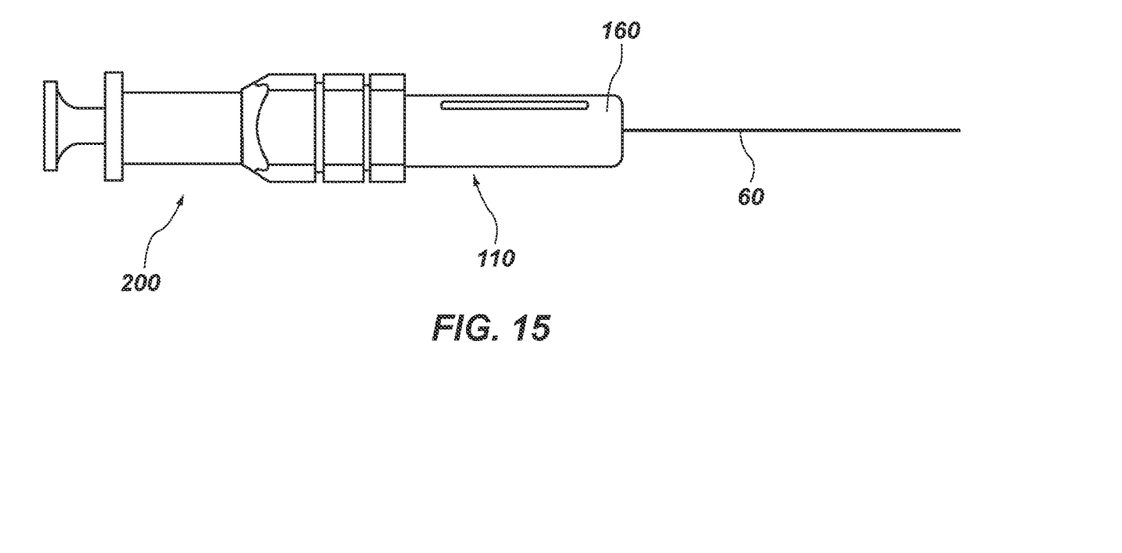
FIG. 15 is a top view of the assembly shown in FIG. 13, illustrating the cover of the needle holder in the closed orientation over the opening of the cradle of the needle holder.
Figure 16:
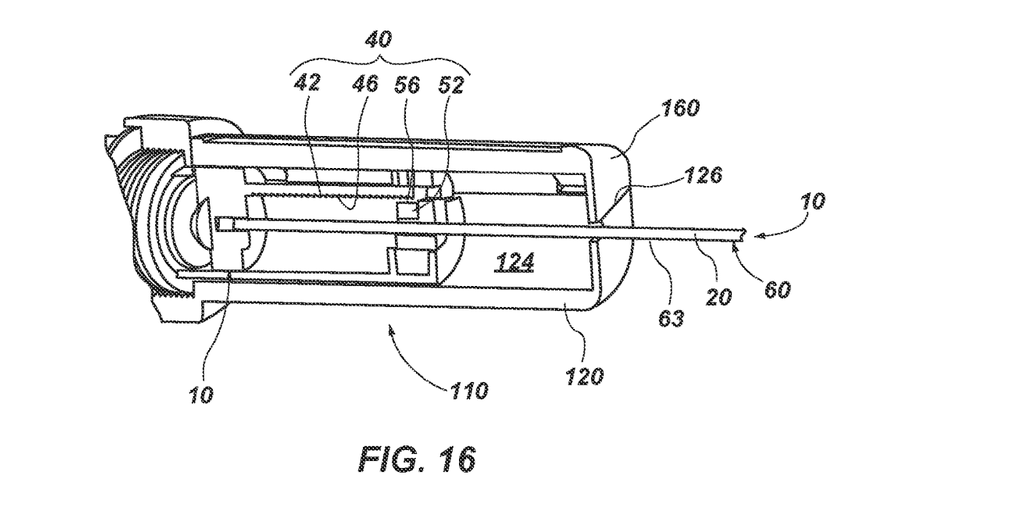
FIG. 16 is a cross-sectional representation of the assembly shown in FIG. 13, with the cover of the needle holder in the closed orientation and the lock of the lockable biopsy needle set in the unlocked position that enables the needle of the lockable biopsy needle set to move relative to the cannula of the lockable biopsy needle set.

Once the biopsy needle set 10 has been properly positioned within the interior 124 of the receptacle 120 of the needle holder 110, as shown in FIGS. 15 and 16, the cover 160 of the needle holder 110 may be moved from its open orientation to its closed orientation. When the cover 160 is closed over the opening 126 and, thus, over the biopsy needle set 10 within the interior 124 of the receptacle 120 of the needle holder 110, the biopsy needle set 10 may be placed in its unlocked arrangement. The biopsy needle set 10 may be placed in its unlocked arrangement when the distal element 52 of the lock 40 is placed in its unlocked orientation, in which the distal element 52 disengages the proximal element 42 of the lock 40, for example, as the teeth 56 of the distal element 52 disengage teeth 46 of the proximal element 42. With the biopsy needle set 10 in its unlocked arrangement, the tissue sampling device 200 may be triggered and the biopsy needle set 10, including its needle 20 and its cannula 60, may be actuated; for example to obtain a sample of tissue from a subject.

Figure 17:
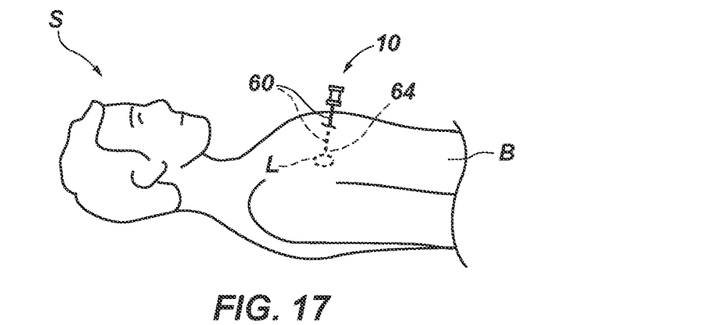
FIGS. 17-19 schematically depict an embodiment of use of the tissue sampling device to manually obtain a tissue sample from a subject.
Figure 18:
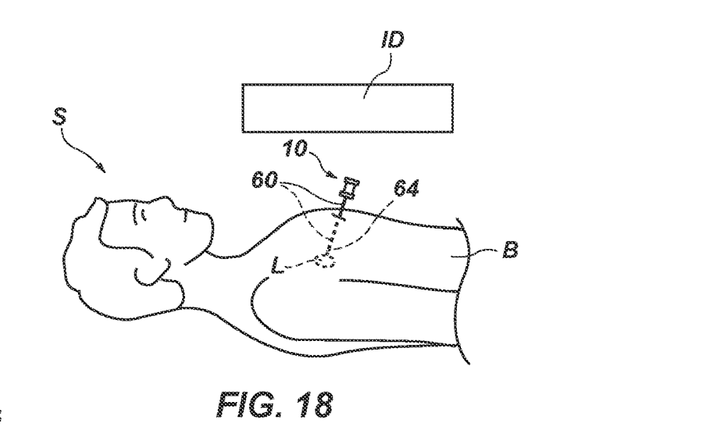
Figure 19:
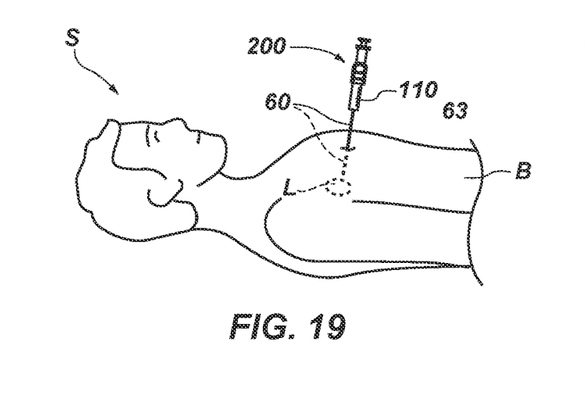

Turning now to FIGS. 17-19, an embodiment of a tissue sampling method is depicted and described. In FIG. 17, a distal tip 64 of a shaft 61 of a cannula 60 (FIG. 1) of a biopsy needle set 10 is introduced into a body B of a subject S at a location L believed to be proximate to tissue that is to be sampled (e.g., biopsied, etc.). Such placement of the distal tip 64 may occur while the biopsy needle set 10 is locked, or in its locked arrangement.

With the distal tip 64 remaining in place within the body B of the subject S, the body B of the subject S, or at least part of the body B, may be imaged with an imaging device ID, as shown in FIG. 18. Any suitable type of imaging may be employed (e.g., fluoroscopy, or x-ray; computed tomography (CT); positron emission tomography (PET); magnetic resonance (MR); etc.). If the imaging reveals that the distal tip 64 has not been properly positioned, the cannula 60 may be repositioned and imaging may be repeated.

When imaging reveals that the distal tip 64 has been properly placed adjacent (e.g., proximal) to the location L of tissue that is to be sampled, the biopsy needle set 10 may be introduced into an interior 124 of a receptacle 120 (FIG. 13) of a needle holder 110 (with a cover 160 (FIG. 13) of the needle holder 110 in an open orientation, of course) on a tissue sampling device 200, as illustrated by FIG. 19. The needle hub 30, the cannula hub 70, and the lock 40 may be placed within the interior 124 of the body 122 of the receptacle 120, as shown in FIGS. 13 and 14. The distal portion 63 of the cannula 60 may protrude through an opening in the distal side of the body 122 of the receptacle 120, as shown in FIGS. 15 and 16. Once the biopsy needle set 10 is properly assembled with the needle holder 110, the cover 160 of the needle holder 110 may be closed over the opening 126 of the receptacle 120, as shown in FIGS. 15 and 17, unlocking the biopsy needle set 10 and enabling use of the tissue sampling device 200 to actuate the biopsy needle set 10 in a manner that will cause the biopsy needle set 10 to obtain a sample of the tissue at the location L of interest.

Once the tissue sampling device 200 and the biopsy needle set 10 have been used to obtain a sample from the location L of interest, the cannula 60 may then be removed from the body B of the subject S, the biopsy needle set 10 may be disassembled from the needle holder (e.g., by opening the cover 160 and pulling the biopsy needle set 10 out of the receptacle 120, etc.), and the sample may be retrieved from the needle 20.

Although the preceding description and the accompanying drawings provide many specifics, these should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. A biopsy gun, comprising:
    a biopsy needle set, including:
        a needle hub;
        a needle protruding distally from the needle hub;
        a cannula hub distal and spaced apart from the needle hub, the needle extending through the cannula hub;
        a cannula protruding distally from the cannula hub, the cannula residing concentrically over the needle; and
        a lock positioned between the needle hub and the cannula hub to prevent unintentional distal movement of the needle hub relative to the cannula hub and unintentional distal movement of the needle; and
    an actuator that controls operation of the biopsy needle set;
    a needle holder at a distal end of the actuator, including:
        a cradle that receives at least the needle hub and the cannula hub of the biopsy needle set;
        a cover having an open position in which the cradle is exposed and a closed position in which the cover covers the cradle, the cover including the actuator that engages the lock of the biopsy needle set when the cover is in the closed position to enable the needle hub to move distally relative to the cannula hub and to enable the needle to move distally.

2. The biopsy gun of claim 1, wherein the actuator of the cover of the needle holder disengages the lock of the biopsy needle set when the cover is in the open position.

3. The biopsy gun of claim 1, wherein the cradle of the needle holder positions the needle hub, the needle, the cannula hub, and the cannula.

4. The biopsy gun of claim 3, wherein the cradle includes a cradle for the needle hub.

5. The biopsy gun of claim 1, wherein the cradle of the needle holder includes an orifice at a distal end thereof through which the needle and the cannula can protrude.

6. The biopsy gun of claim 1, wherein the lock of the biopsy needle set comprises a ratcheting mechanism.

7. The biopsy gun of claim 6, wherein the ratcheting mechanism includes:
    an elongated element that extends distally from the needle hub; and
    a locking element associated with the cannula hub, the locking element including a channel through which the elongated element extends, the locking element including a locked position in which the channel engages the elongated element and an unlocked position in which the channel disengages the elongated element.

8. The biopsy gun of claim 7, wherein the locking element is slidingly assembled with the cannula hub.

9. The biopsy gun of claim 8, wherein the elongated element includes teeth and the locking element includes at least one tooth capable of engaging the teeth of the elongated element with the locking element in the locked position.

10. The biopsy gun of claim 1, wherein the lock includes a biased lock that holds the lock in a locked arrangement.

11. The biopsy gun of claim 10, wherein the biased lock comprises a spring.

12. The biopsy gun of claim 10, wherein the actuator of the cover of the needle holder, when the cover is placed in the closed position, overcomes a biasing force of the spring to force the lock into an unlocked arrangement.

13. The biopsy gun of claim 1, wherein a proximal end of the needle holder is fixedly secured to the distal end of the actuator.

14. The biopsy gun of claim 13, wherein the proximal end of the needle holder includes threads that engage complementary threads of the distal end of the actuator.

15. A biopsy needle set, including:
    a needle hub;
    a needle protruding distally from the needle hub;
    a cannula hub distal and spaced apart from to the needle hub, the needle extending through the cannula hub;
    a cannula protruding distally from the cannula hub, the cannula residing concentrically over the needle; and
    a lock comprising a ratcheting mechanism positioned at least partially between the needle hub and the cannula hub to prevent unintentional distal movement of the needle hub relative to the cannula hub and unintentional distal movement of the needle, the ratcheting mechanism including:
        an elongated element that extends distally from the needle hub; and
        a locking element slidingly assembled with the cannula hub, the locking element including a channel through which the elongated element extends, the locking element including a locked position in which the channel engages the elongated element and an unlocked position in which the channel disengages the elongated element, the locking element biased to hold the lock in a locked arrangement.

16. The biopsy needle set of claim 15, wherein the elongated element includes teeth and the locking element includes at least one tooth capable of engaging the teeth of the elongated element with the locking element in the locked position.

17. A method for obtaining a tissue sample from a subject, comprising:
    introducing a distal tip of a cannula of a biopsy needle set into a body of a subject at or adjacent to a location of interest while a longitudinal position of a needle of the biopsy needle set is locked into place relative to a longitudinal position of the cannula;
    imaging the body of the subject to confirm that the distal tip of the cannula has been properly positioned at or adjacent to the location of interest;
    upon confirming that the distal tip of the cannula has been properly positioned, introducing a needle hub, a cannula hub, and a lock into a receptacle of a needle holder of a tissue sampling device;

closing a cover of the needle holder over the needle hub, the cannula hub, and the lock, including engaging the lock to unlock the longitudinal position of the needle relative to the longitudinal position of the cannula; and using the tissue sampling device to actuate the needle and the cannula to obtain a sample from the location of interest.

18. The method of claim 17, further comprising:

repositioning the distal tip of the cannula if imaging shows that the distal tip of the cannula is not properly positioned; and reimaging the body of the subject to confirm that the distal tip of the cannula has been properly positioned.

19. The method of claim 17, further comprising:

removing the cannula and the needle from the body of the subject;

removing the biopsy needle set from the needle holder; and removing the sample from the needle.

\* \* \* \* \*